US006428461B1

(12) United States Patent

Marquez et al.

(10) Patent No.: US 6,428,461 B1
(45) Date of Patent: Aug. 6, 2002

(54) METHOD FOR INHIBITING OXIDATION OF POLYUNSATURATED LIPIDS

(75) Inventors: Manuel Marquez, Prospect Heights; Ahmad Akashe, Mundelein, both of IL (US)

(73) Assignee: Kraft Foods Holdings, Inc., Northfield, IL (US)

(*) Notice: Subject to any disclaimer, the term of this patent is extended or adjusted under 35 U.S.C. 154(b) by 0 days.

(21) Appl. No.: 09/841,878

(22) Filed: Apr. 24, 2001

(51) Int. Cl.[7] .............................. C07C 1/00; C11B 5/00
(52) U.S. Cl. .............................. 584/5; 426/541
(58) Field of Search .............................. 584/5; 426/541

(56) References Cited

U.S. PATENT DOCUMENTS

| | | | |
|---|---|---|---|
| 4,253,848 | A | 3/1981 | Porter |
| 4,957,757 | A | 9/1990 | Law et al. |
| 4,975,290 | A | 12/1990 | Artz et al. |
| 5,015,483 | A | 5/1991 | Haynes et al. |
| 5,077,069 | A | 12/1991 | Chang et al. |
| 5,118,665 | A | 6/1992 | Pickart |
| 5,230,916 | A | 7/1993 | Chang et al. |
| 5,304,679 | A | 4/1994 | McEvily et al. |
| 5,733,524 | A | 3/1998 | Bucala et al. |
| 5,801,200 | A | 9/1998 | Bucala et al. |
| 5,891,491 | A | 4/1999 | Owens et al. |

FOREIGN PATENT DOCUMENTS

| | | | |
|---|---|---|---|
| EP | 209509 | * | 1/1987 |
| EP | 0 209 509 | | 9/1991 |
| JP | 6-305956 | | 11/1994 |

* cited by examiner

*Primary Examiner*—Deborah D. Carr
(74) *Attorney, Agent, or Firm*—Fitch, Even, Tabin & Flannery

(57) ABSTRACT

The present invention generally relates to inhibition of oxidation of polyunsaturated lipids by mixing the polyunsaturated lipids with a combination of polyamines providing a unique anti-oxidative effect on the polyunsaturated lipids. A especially advantageous combination of polyamines used in this regard includes spermine and a different linear aliphatic polyamine, such as spermidine, putrescine, or mixtures thereof. The rate of off-flavor development is significantly reduced in polyunsaturated lipids blended with such combinations of different polyamines. In addition, polyunsaturated lipid-containing materials and compositions can be stabilized using edible, non-toxic anti-oxidants based on such polyamine combinations. Omega-3 fatty acids and compositions containing them are especially well-suited for processing in this manner. The stabilized polyunsaturated lipid-containing products obtained in this manner have extended shelf-life while permitting the health and nutritional value of the treated lipids to be more fully accessed.

38 Claims, 2 Drawing Sheets

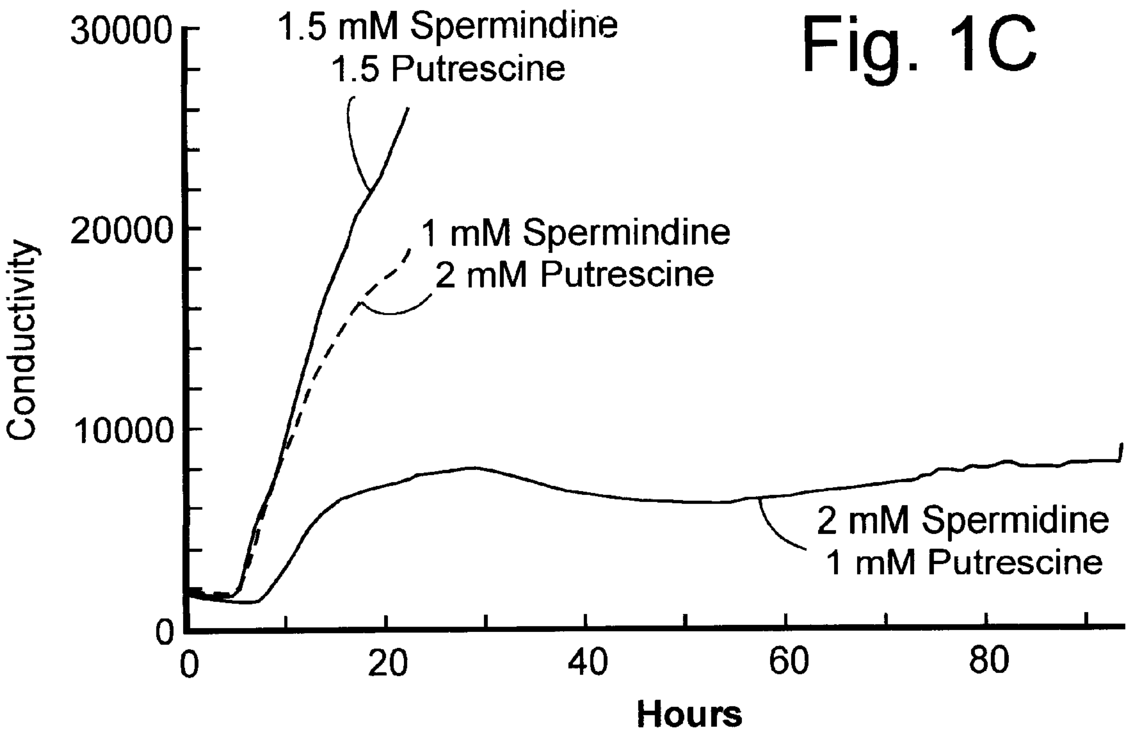
Fig. 1C
Fig. 2
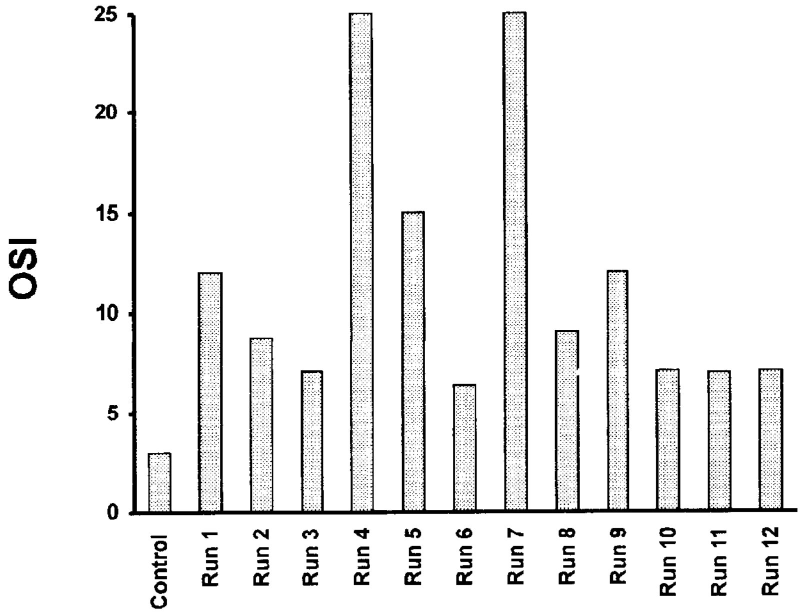

METHOD FOR INHIBITING OXIDATION OF POLYUNSATURATED LIPIDS

FIELD OF THE INVENTION

The present invention generally relates to a method for inhibiting the oxidation of polyunsaturated lipids using uniquely effective combinations of two or more polyamines, and the stabilized products obtained therefrom.

BACKGROUND OF THE INVENTION

Recent trends in food processing and preparation include efforts to reduce the saturated fatty acid content of many foods in favor of unsaturated fatty acids. Among other things, the replacement of saturated fats in a diet with polyunsaturated fats can help to reduce cholesterol levels.

Omega-3 long chain polyunsaturated fatty acids. in particular, have been viewed as highly attractive potential additives for foods and dietary supplements. Omega-3 polyunsaturated fatty acids are found naturally in marine oils, and also in certain vegetable oils. Certain fish oils, such as capelin oil, cod liver oil, and menhaden oil, contain large amounts of highly unsaturated long chain fatty acids, such as eicosapentaenoic acid (EPA), docosahexaenoic (DHA), and eicosatetraenoic acid (arachidonic acid). EPA and DHA are omega-3 fatty acids. Many vegetable oils contain linoleic acid, an essential fatty acid, which is classified as an omega-6 fatty acid. However, unlike many other vegetable oils, flaxseed oil also contains significant amounts (generally about 55 to about 65 percent) alpha linolenic acid (ALA), which is another essential fatty acid. ALA also is an omega-3 fatty acid. Small amounts of ALA also can be found, for example, in walnut oil, canola oil, soybean oil, and black currant. The body metabolizes ALA, at least in part, into EPA, and, to a lesser extent, DHA and 3-series prostaglandins.

The omega-3 fatty acids obtained directly from fish oils (i.e., EPA and DHA) are thought to offer a wide range of possible nutritional and health benefits. These benefits include reductions in cholesterol levels, anti-thrombotic effects, anti-arthritic effects in joints, and enhancement of mental and visual acuity. ALA has been reported to be useful in lowering blood pressure, controlling inflammatory conditions, inhibiting autoimmune reactions, and protecting against cardiovascular disease.

While foods and dietary supplements prepared with such polyunsaturated fatty acids may be healthier, they also have an increased vulnerability to rancidity. Rancidity in lipids, such as unsaturated fatty acids, is associated with oxidation off-flavor development. The off-flavor development involves food deterioration affecting flavor, aroma, color, texture, and the nutritional value of the particular food. A primary source of off-flavor development in lipids, and consequently the products that contain them, is the chemical reaction of lipids with oxygen. The rate at which this oxidation reaction proceeds has generally been understood to be affected by factors such as temperature, degree of unsaturation of the lipids, oxygen level, ultraviolet light exposure, presence of trace amounts of pro-oxidant metals (such as iron, copper, or nickel), lipoxidase enzymes, and so forth.

From the standpoint of food oxidation, the relevant lipids are compounds containing unsaturated fatty acids. Hydroperoxides are the major initial reaction products of the oxidation of the unsaturated fatty acids. The hydroperoxides are unstable, highly reactive intermediates, which can be responsible for the off-flavor development themselves, or as they further decompose, they form volatile aldehydes or ketones responsible for strong unpleasant smell and taste. In addition, free radicals formed during oxidation of the unsaturated fatty acids may participate in the development of arteriosclerosis and other pernicious diseases in the consumer.

The susceptibility and rate of oxidation of the unsaturated fatty acids can rise dramatically as a function of increasing degree of unsaturation in particular. In this regard, EPA and DHA contains five and six double bonds, respectively. This high level of unsaturation renders the omega-3 fatty acid fish oils readily oxidizable. The natural instability of such fish oils gives rise to their unpleasant odor and unsavory flavor characteristics where oxidation of the fish oils has occurred, even after a relatively short period of storage time. The odor and flavor of rancid fish oils are strong and pungent. Consequently, elimination of these odors and tastes, once generated, has been difficult if not impossible. Moreover, the off-flavor odor or taste can be so malodorous that even a small level of rancidity in a fish oil-containing product can be negatively perceived by a consumer. Linolenic acid (ALA) derived from plant oils is also very susceptible to off-flavor development. Dietary supplements containing omega-3 oils often are packaged in dark, light-blocking containers in either encapsulated form; free liquid forms generally require chilled storage once opened. Despite such precautions, they still tend to have a strong fish-like flavor and/or smell. Consequently, it has been very difficult in the past to produce omega-3 fatty acid containing products or supplements having an extended shelf life.

Previous proposals or practices for addressing lipid oxidation include, for example, U.S. Pat. No. 4,975,290 which describe a method of inhibiting lipid oxidation in food products such as uncured meat and extruded food products using an aqueous solution of organic iron salt. U.S. Pat. No. 5,015,483 describes means for stabilizing oxidizable lipophilic components such as fish oils by encapsulation of the components in a lipidic bilayer of liposomes (preferably saturated phospholipids). U.S. Pat. No. 5,077,069 describes use of natural antioxidants including tocopherols, ascorbic acid, citric acid, and phospholipids, and optionally rosemary extract, for stabilizing polyunsaturated oils. U.S. Pat. No. 5,230,916 describes use of an ascorbic acid complex for stabilizing polyunsaturated oils. U.S. Pat. No. 5,304,679 describes a composition for inhibiting the enzymatic browning of foods and beverages by using certain resorcinol-derivatives in place of earlier enzymatic browning inhibitors such as sodium bisulfite. U.S. Pat. No. 5,891,491 describes use of certain dihydroxyquinoline compounds to extend the shelf life of products derived from mammals and fish fed a diet including such compounds. Also, EPO 0 209 509 describes protecting easily oxidizable compounds, especially polyunsaturated fatty acids, against oxidation, in which the anti-oxidant is a compound containing primary or secondary amino-groups linked to carbon in an aliphatic residue of a certain described formula. The antioxidants are specifically characterized therein as being either spermine or spermidine. Also, comparative reference is made to BHA (butylated hydroxyanisole) and TBHQ (tertiary butylhydroquinone) as anti-oxidants. Although not directed to anti-oxidants for lipids, Japanese Pat. Publ. Kokai No. 6-305956 describes a protein absorption enhancing agent containing a polyamine as the active component, and a nutrient composition containing the polyamine and food components such as artificial milk powder formulas. Spermine individually is characterized therein as being particularly effective as the polyamine active agent for the protein absorption enhancing function.

Despite these prior proposals, there still remains a need for commercially viable approaches to fully realize the health and nutritional benefits of foods or supplements containing omega-3 oils and other beneficial polyunsaturated fatty acids. In particular, there remains a need for advanced, cost-effective and safe measures which can significantly impede the rates at which such polyunsaturated fatty acids and products containing them become rancid. The present invention fulfills these needs, as well as other needs and objectives, by a method for processing unsaturated lipids by contacting them with a uniquely effective combination of tow or more polyamines.

SUMMARY OF THE INVENTION

The present invention provides a method for treating polyunsaturated lipids by blending them with at least two different polyamines in amounts effective to induce a unique inhibitory effect on the rate of oxidative rancidity of the polyunsaturated lipids. The polyunsaturated lipids processed according to this invention have a significantly reduced rate of off-flavor development, which translates into increased shelf-life for the polyunsaturated lipids and any products containing them.

The effective amounts of the different polyamines used in combination with the polyunsaturated lipid in the practice of this invention can vary depending on the types of the polyamines and polyunsaturated lipid involved in the combination, as long as the respective amounts of the different polyamines are sufficient, in combination, to reduce the rate of oxidative rancidity of the polyunsaturated lipid. As demonstrated by experimental data discussed in more detail below, this reduction in the rate of oxidative rancidity is manifested as a greater increase in the oxidative stability of the polyunsaturated lipid or composition containing the lipid blended with the combination of polyamines according to the invention, as compared to the same lipid treated with a single polyamine of the combination at the same overall polyamine concentration. For purposes herein, the oxidative stability parameter is measured as an oil stability index (OSI) value at a given temperature. The OSI is an accelerated rancidity test, described in more detail hereinafter, that measures the rate of oxidation of a oil or fat. It is expressed as a numerical index value. The higher the index value, at a given temperature, the more stable the oil or product containing same is to oxidation. The OSI value observed for polyunsaturated lipids treated according to the invention with the combination of different polyamines is significantly greater than that observed for the same lipid except as treated with only one of the polyamines at the same overall concentration level.

Generally, the practice of this invention allows the $OSI_{110}$ value (i.e., the OSI value as measured at 110° C.) of a polyunsaturated lipid treated with a combined amount of two or more polyamines according to the invention to increase, on average, about two fold or more, preferably about three fold or more, and more preferably about five fold or more, than the $OSI_{110}$ value of the same polyunsaturated lipid where treated with an equivalent concentration of either of polyamine ingredients alone. As a result, the combination of the polyamines used in treating polyunsaturated lipids according to this invention can effectively retard oxidation and off-flavor development in polyunsaturated lipids.

To accomplish this advantageous effect of the invention, each of the different polyamine ingredients is generally mixed with polyunsaturated lipid in an amount of at least about 0.25 millimoles (mM), preferably at least about 0.5 mM, and more preferably at least about 1.5 mM. Generally, the total amount of the two or more polyamines is about 0.5 to about 9 mM, preferably about 1 to about 6 mM, and more preferably about 1.5 to about 3 mM.

The polyamines suitable for treating the polyunsaturated lipids according to this invention, generally include linear aliphatic polyamines. The different polyamines, which are combined together, can be generally represented by the general formula:

$$H_2N-[(CH_2)_p-(NH)_q-(CH_2)_r-(NH)_s-(CH_2)_t]_u-NH_2$$

wherein u is an integer of 1 to 5; p, r, and t independently are integers of 0 to 8, with the proviso that at least one of p, r, and t is greater than or equal to 2; wherein q and s independently are 0 or 1, with the proviso that at least one of u, p, r, t, q, and s has a different integer value in the first polyamine than in the second polyamine.

In a preferred aspect of the invention, the combination of polyamines includes spermine used in combination with spermidine, putrescine, or mixtures thereof. These linear, aliphatic polyamines are biocompatible, naturally occurring polyamines which are well-suited for food products and dietary supplement applications. Generally the polyunsaturated lipid is blended with a polyamine composition containing about 10 percent to about 90 percent of spermine and about 10 percent to about 90 percent of the second polyamine; preferably, the polyamine composition contains about 40 to about 60 percent of spermine and about 40 percent to about 60 percent of the second polyamine. In other words, the ratio of spermine to the second polyamine is generally about 1:9 to about 9:1 and preferably about 2:3 to about 3:2. In a preferred aspect of the invention, the polyunsaturated lipid treated according to the invention is a polyunsaturated fatty acid, and more preferably is an omega-3 fatty acid.

In one advantageous aspect of the invention, the present invention fulfills a vital commercial need for rancidity-inhibiting measures suited for omega-3 fatty acids, in which the protection measures are based on edible (food-friendly) additives, namely, the use of combined polyamines as described herein. Suitable omega-3 fatty acids include eicosatetraenoic acid (EPA), docosahexaenoic acid (DHA), alpha linolenic acid (ALA), and mixtures thereof. The present invention permits the considerable potential health benefits available in fish oils and vegetable oils that contain omega-3 fatty acids to be more fully accessed, while significantly increasing the shelf-life of such products. Moreover, due to the increased shelf-life attained, the omega-3 fatty acid containing oils processed according to the invention can be used as substitutes for saturated fats in food products or as a nutritional supplement taken separately or as added to foods or beverages.

Although the polyamine-treated polyunsaturated lipids prepared according to this invention are suitable for food products in particular, they are not necessarily limited thereto. They also could be used in other applications involving polyunsaturated lipid content including, for example, cosmetics, medicinal or cosmetic topical ointments, medicinal or cosmetic topical lotions, medicinal or cosmetic topical creams, personal care products, and the like.

BRIEF DESCRIPTION OF THE DRAWINGS

Other features, and advantages of the present invention will become apparent from the following detail description of preferred embodiments of the invention with reference to the drawings, in which:

FIGS. 1A, 1B, and 1C are graphs from which oil stability index (OSI) values were determined on an oxidation stability instrument at 110° C. for a series of sample runs and a control containing flaxseed oil and varying amounts of one or more polyamines prepared according to the method of Example 1, in which the various curve plots shown were generated from measurements of conductivity taken over time.

FIG. 2 is a bar graph showing the OSI value results obtained for the series of sample runs and control containing flaxseed oil and varying amounts of one or more polyamines prepared according to the method of Example 1.

DETAILED DESCRIPTION OF THE INVENTION

Figure 1A:
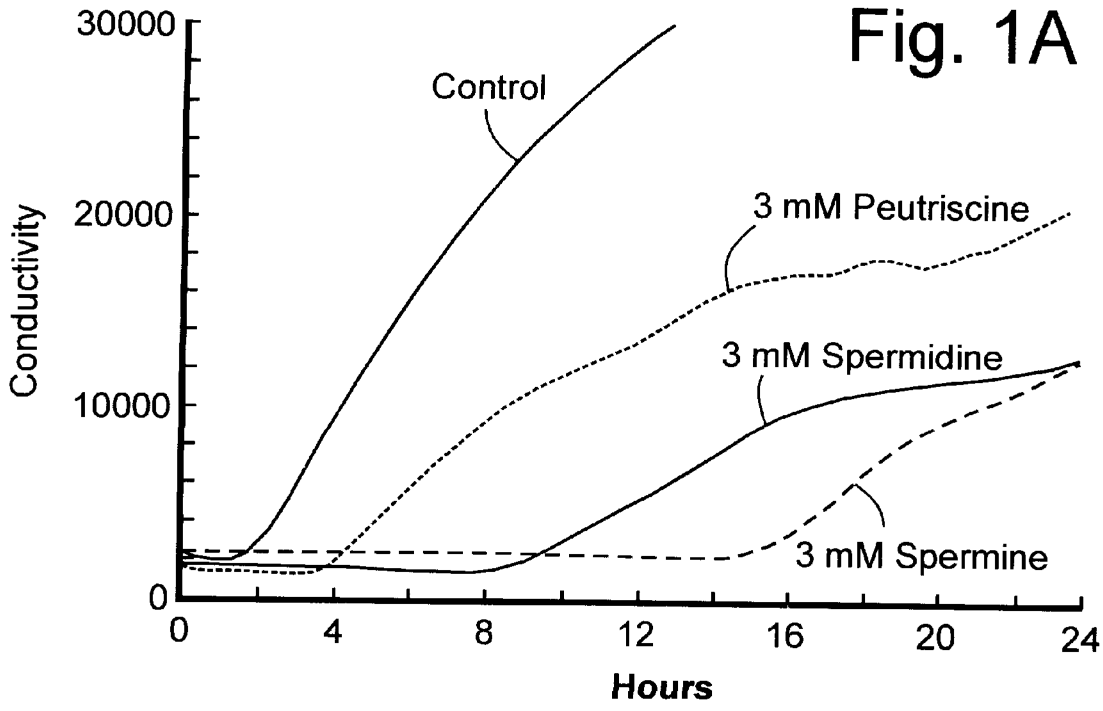

Generally, the present invention provides a method for processing polyunsaturated lipids by their direct physical admixture with a combination of polyamines in respective amounts effective such that the resulting treated lipid experiences an increase in oxidative stability, such as measured as an OSI value, which exceeds that possible by blending the same lipid with only one of the polyamines at the same overall concentration. The invention also is directed to the product of that method.

Polyunsaturated lipids that can be treated with the polyamine combinations according to the present invention include, for example, polyunsaturated fatty acids, and preferably long chain polyunsaturated fatty acids having 18 to 22 carbons in the main chain. The fatty acid chains in these fatty acids can be straight, branched, or ring structures. Preferably, the fatty acid chains are straight hydrocarbon chains having cis configurations at the carbon-carbon double bonds along the main chains. Suitable polyunsaturated fatty acids for use in this invention can be obtained from natural sources or can be prepared synthetically. Natural sources of suitable polyunsaturated lipids include readily available vegetable, animal, and marine oils containing long chain polyunsaturated fatty acids. Polyunsaturated fatty acids are present in significant amounts, for example, in flaxseed oil, corn oil, sunflower oil, cottonseed oil, canola oil, soybean oil, tung oil, lard, cod liver oil, capelin oil, menhaden oil, and so forth.

Examples of suitable polyunsaturated fatty acids (i.e., fatty acids containing two or more carbon-carbon double bonds) include linoleic (e.g., 9,12-octadecadienoic acid), linolenic acid (9,12,15-octadecatrienoic acid), arachidonic acid (5,8,11,14-eicosatetraenoic acid), EPA (5,8,11,14,17-eicosapentaenoic acid), and DHA (4,7,10,13,16,1 9-docosahexaenoic). All the carbon-carbon double bonds in these fatty acids will typically be in the cis configuration. Trans and positional isomers of the above-exemplified polyunsaturated fatty acids are also possible, although the trans isomers are not preferred due to possible unfavorable health issues associated with them. The omega-3 fatty acids, such as EPA, DHA, and ALA, are a preferred polyunsaturated lipid for treatment according to an aspect of this invention in light of the widely recognized health benefits associated with these fatty acids, which makes them an attractive food additive and ingredient, among other things.

ALA is present, for example, in a variety of vegetable oils including flaxseed oil, soybean oil, canola oil, walnut oil, and black currant. In that linseed oil is the oil extracted from flax, the terms flaxseed oil and linseed oil can be used interchangeably for purposes of this application. EPA and DHA are present, for example, in certain fish oils, such as capelin oil, cod liver oil, and menhaden oil. Fish oils are commercially available containing approximately 25 percent EPA and DHA.

In order to synergistically increase the OSI value of the polyunsaturated fatty acids, the fatty acids are mixed with polyamine combinations according to this invention. To accomplish this advantageous effect of the invention, each of the different polyamine ingredients is generally mixed with polyunsaturated lipid in an amount of at least about 0.25 mM, preferably at least about 0.5 mM, and more preferably at least about 1.5 mM. Generally, the total amount of the two or more polyamines is about 0.5 to about 9 mM, preferably about 1 to about 6 mM, and more preferably about 1.5 to about 3 mM.

In one advantageous aspect of the invention, the polyamines are linear aliphatic polyamines, albeit a combination of two or more different such polyamines. The polyamines are different in the sense that they are non-identical from the perspective of molecular structure.

In one aspect of the invention, the different polyamines, which are combined together, each can be generally represented the general formula:

$$H_2N—[(CH_2)_p—(NH)_q—(CH_2)_r—(NH)_s—(CH_2)_t]_u—NH_2$$

wherein u is an integer of 1 to 5; p, r, and t independently are integers of 0 to 8, with the proviso that at least one of p, r, and t is greater than or equal to 2; wherein q and s independently are 0 or 1, with the proviso that at least one of u, p, r, t, q, and s has a different integer value in the first polyamine than in the second polyamine.

Suitable aliphatic polyamines include, for example, alkylene diamines, alkylene triamines, alkylene tetraamines, alkylene pentamines, alkylene hexamines, iminobis alkylamines, and so forth. Illustrative, non-limiting examples of suitable aliphatic polyamines include ethylenediamine, diethylenetriamine, triethylenetetraamine, pentaethylenehexamine, spermine ($H_2NCH_2CH_2CH_2NHCH_2CH_2CH_2CH_2NHCH_2CH_2CH_2NH_2$), putrescine ($H_2NCH_2CH_2CH_2CH_2NH_2$), cadaverine ($H_2NCH_2CH_2CH_2CH_2CH_2NH_2$), spermidine ($H_2NCH_2CH_2CH_2CH_2NHCH_2CH_2CH_2NH_2$), iminobis ethylamine, iminobis propylamine, N-(3-aminopropyl)-1,3-propanediamine, 1,3-diaminopropane, 1,4-diaminobutane, N,N'-bis(3-aminopropyl)-1,3-propanediamine, and the like. Substituted variants of these polyamines are possible, but generally not preferred or necessary in the practice of this invention.

Preferred polyamines to be used in combination in practicing this invention are edible and generally non-toxic when used at levels inducing the inventive effect described herein insofar as increasing the oxidative stability of a polyunsaturated fatty acid. In one preferred aspect, the combination of polyamines includes spermine used in combination with spermidine or putrescine, or mixtures thereof. These linear, aliphatic polyamines are biocompatible, naturally occurring polyamines, which are well-suited for food products and dietary supplement applications. The blending of a polyunsaturated lipid with a polyamine combination including spermine generally involves adding thereto a polyamine composition containing about 10 percent to about 90 percent of spermine and about 10 percent to about 90 percent of the second polyamine; preferably, the polyamine composition contains about 40 to about 60 percent of spermine and about 40 percent to about 60 percent of the second polyamine. In other words, the ratio of spermine to the second polyamine is generally about 1:9 to about 9:1 and preferably about 2:3 to about 3:2.

Numerous commercial sources exist for polyamines identified herein as being suitable in the practice of the invention. Also, certain naturally-occurring linear aliphatic polyamines, such as spermine and others, can be extracted from whey protein concentrates obtained from the production of cheese from milk. Such polyamines in whey protein concentrate can be isolated by ultrafiltration using a cation-exchange resin that selectively adsorbs polyamines, which are then eluted with an acid or salt solution, followed by neutralization to obtain a polyamine solution. Polyamines can be characterized by, for example, gas chromatographic or other techniques known in the art.

The polyamines suitable for use in this invention generally are liquids at room temperature (i.e., about 20–30° C.). The polyunsaturated lipids suitable for treatment by the polyamines also typically are liquids at room temperature, especially in the case of polyunsaturated fatty acids. If not, the polyunsaturated lipids can be heated sufficient to liquefy the material to facilitate thorough blending and mixing of the lipid with the combination of polyamines.

The polyamines and lipid can be combined in any suitable vessel or container of sufficient holding volume space. Generally no special handling precautions or measures are needed. Also, the description herein of the different polyamines as being used in combination does not imply that the different polyamines must be combined together before admixture to the polyunsaturated lipid to be treated. These ingredients can be combined in any convenient sequence or combination. Preferably, these ingredients, once combined, are thorough mixed sufficient to provide an essentially uniform dispersion or mixture of the ingredients in the mixture.

The oxidative stability of the polyunsaturated lipid/polyamine combination mixtures can be assessed as an OSI value measured with a commercially available oxidation stability instrument such as those that can be obtained from Omnion Inc., Rockland, Mass. The OSI values are preferably determined at above room temperature conditions (i.e., under accelerated test conditions). By comparing the OSI value of an untreated lipid of interest, a single polyamine treated version, and the polyamine combination-treated version according to this invention, differences and changes in the OSI value can be compared to confirm the suitable polyamine combinations for treatment of the polyunsaturated lipids.

Generally, the practice of this invention allows the $OSI_{110}$ value of a polyunsaturated lipid treated with a combined amount of two or more polyamines according to the invention to increase, on average, about two fold or more, preferably about three fold or more, and more preferably about five fold or more, than the $OSI_{110}$ value of the same polyunsaturated lipid where treated with an equal total amount of any one of the polyamine ingredients. Although the OSI values reported herein were generally obtained at 110° C., other temperatures could of course be used.

Other materials and additives which can be included in the same food products treated by the polyamine combination according to this invention are, for example, preservatives; lipid soluble vitamins; glycerol; acidulants; flavorants; conventional antioxidants such as tocopherol, ascorbic acid, citric acid, monosodium glutamate, sulfites; UV absorbers; and the like.

Although the polyamine-treated polyunsaturated lipids prepared according to this invention are especially suitable for food products in particular, they are not necessarily limited thereto. They also could be used in other applications involving polyunsaturated lipid content including, for example, cosmetics, medicinal or cosmetic topical ointments, medicinal or cosmetic topical lotions, medicinal or cosmetic topical creams, personal care products, and the like.

The Examples that follow are intended to illustrate, and not to limit, the invention. All ratios and percentages used herein are by weight, unless otherwise indicated.

EXAMPLE 1

Separate samples of flaxseed oil were admixed with an additive composed either of a single polyamine or combinations of at least two polyamines, which are described as runs 1–12 in Table 1, to demonstrate the effect of using combinations of different polyamine additives on the oxidative stability of the oil. The polyamines tested were spermine, spermidine, and putrescine.

For each of sample runs 1–12, 3.0 millimoles (mM) total of an individual polyamine or combination of the polyamines, as indicated in Table 1, was blended into 5 mL flax seed oil (bio-original), and the components were mixed thoroughly at room temperature (about 25° C.).

The flaxseed oil was obtained from Bioriginal Food and Science Corp., Saskatchewan, Canada. The flaxseed oil contained about 4.5 to 6.4 percent palmitic acid (C 16:0), about 14.3 to 23.9 percent oleic acid (C 18:1), about 12.1 to 17.7 percent linoleic acid (C 18:2), and about 50 to 60 percent linolenic acid (C 18:3). As supplied, the flaxseed oil did not contain any extraneous anti-oxidant additives. A sample of the flaxseed oil without added polyamine was included as a control run C1.

Figure 1B:
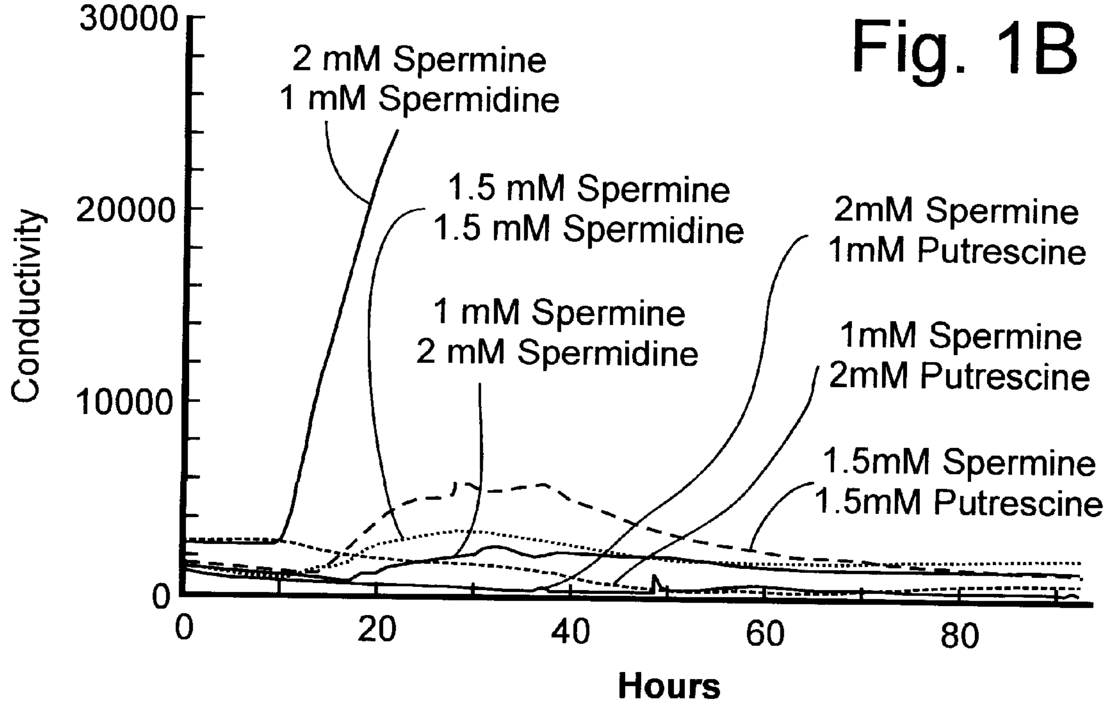

To measure the oxidative stability of each of the oil/polyamine mixtures of runs 1–12 and also control C1, 5 g of a flaxseed oil/polyamine mixture or the oil control was loaded into a glass tube equipped with an air inlet and outlet. The outlet was connected to a second glass tube containing distilled water. Air was bubbled through the test sample and then passed into the second glass tube under the surface of the distilled water. The second glass tube was contained in the loading well of an OSI instrument manufactured by Omnion Inc., Rockland, Mass. The oil/polyamine mixture was automatically analyzed for oxidative stability in the instrument by bubbling air at a constant rate through the sample at constant temperature of 110° C. As can be appreciated, this oil stability index (OSI) test represented an accelerated test of oxidative stability. The time at which the air introduction commenced was recorded by the instrument. A volatile decomposition product (i.e., formic acid) produced from the oxidative degradation of the oil-containing sample was conveyed into distilled water contained in the second glass tube (i.e., a cell receptacle). The OSI instrument continuously monitored conductivity in the distilled water. The period of time required after which air introduction was commenced until the conductivity rises sharply in the distilled water (i.e., the point of oxidative failure or endpoint) was determined and recorded in hours. The OSI instrument stored the conductivity and run time data, which was plotted in graphs as conductivity measurements versus the monitoring time. Table 1 sets forth the oxidative stability results obtained for all the runs and control as determined in this manner. FIGS. 1A–1C provides the data in graphical form for the sample runs 1–12 and control C1 described in Table 1.

TABLE 1

| | Added Polyamines (mM) | | | OSI |
|---|---|---|---|---|
| Run | spermine | spermidine | putrescine | (HRS) |
| C1 | 0 | 0 | 0 | 2.8 |
| 1 | 3 | 0 | 0 | 16.8 |
| 2 | 0 | 3 | 0 | 11.5 |
| 3 | 0 | 0 | 3 | 6.0 |
| 4 | 2.0 | 1 | 0 | 11.1 |
| 5 | 1.5 | 1.5 | 0 | 18.0 |
| 6 | 1 | 2 | 0 | 25.0 |
| 7 | 2 | 0 | 1 | >90.0 |
| 8 | 1.5 | 0 | 1.5 | 18.0 |
| 9 | 1 | 0 | 2 | >90.0 |
| 10 | 0 | 2 | 1 | 7.0 |
| 11 | 0 | 1.5 | 1.5 | 6.0 |
| 12 | 0 | 1 | 2 | 6.0 |

The above results revealed and demonstrated that an increased antioxidant activity was obtained in the flaxseed oil by introduction therein of a combination of spermine with a second aliphatic polyamine that was not predictable from the effect of either one of the polyamines used alone to treat the same polyunsaturated lipid. Also, combinations of the polyamines which did not include spermine did not yield the significant increase in oxidative stability seen with spermine-containing polyamine combinations, indicating that the presence of spermine as one of the different polyamines had significance. Also, addition of the same polyamines individually to the flaxseed did not demonstrate the anti-oxidation effect to the extent as it was seen with the combination of spermine and a second polyamine.

EXAMPLE 2

The experiment of Example 1 was repeated using the same essentially the same experimental procedure. The results are indicated in Table 2 and graphically shown in FIG. 2.

TABLE 2

| | Added Polyamines (mM) | | | OSI |
|---|---|---|---|---|
| Run | spermine | spermidine | putrescine | (HRS) |
| C2 | 0 | 0 | 0 | 3.0 |
| 13 | 3 | 0 | 0 | 12.0 |
| 14 | 0 | 3 | 0 | 8.7 |
| 15 | 0 | 0 | 3 | 7.0 |
| 16 | 2 | 1 | 0 | >23.0 |
| 17 | 1.5 | 1.5 | 0 | 15.0 |
| 18 | 1 | 2 | 0 | 6.3 |
| 19 | 2 | 0 | 1 | >22.0 |
| 20 | 1.5 | 0 | 1.5 | 9.0 |
| 21 | 1 | 0 | 2 | 12.0 |
| 22 | 0 | 2 | 1 | 7.0 |
| 23 | 0 | 1.5 | 1.5 | 6.9 |
| 24 | 0 | 1 | 2 | 7.0 |

The above results again reveal that a synergistic antioxidant activity achieved in flaxseed oil was attributable to the introduction therein of a combination of spermine with a second aliphatic polyamine. Combinations of the polyamines which did not include spermine did not yield the significant increase in oxidative stability seen with spermine-containing polyamine combinations. Also, addition of the same polyamines individually to the flaxseed did not demonstrate the anti-oxidation effect to the extent as it was seen with the combination of spermine and a second polyamine.

While the invention has been described in terms of preferred embodiments, those skilled in the art will recognize that the invention can be practiced with modification within the spirit and scope of the appended claims.

What is claimed is:

1. A method to reduce the rate of oxidative rancidity of a polyunsaturated lipid comprising blending a polyunsaturated lipid with a first polyamine and a second polyamine, different from the first polyamine, in amounts effective for reducing the rate of oxidative rancidity of the polyunsaturated lipid.

2. The method as recited in claim 1, wherein the first polyamine and second polyamine are independently represented the general formula:

$$H_2N—[(CH_2)_p—(NH)_q—(CH_2)_r—(NH)_s—(CH_2)_t]_u—H_2$$

wherein u is an integer of 1 to 5; p, r, and t independently are integers of 0 to 8, with the proviso that at least one of p, r, and t is greater than or equal to 2; wherein q and s independently are 0 or 1, with the proviso that at least one of u, p, r, t, q, and s has a different integer value in the first polyamine than in the second polyamine.

3. The method as recited in claim 1, wherein the blending comprises adding at least about 0.25 mM of each of the first and second polyamines.

4. The method as recited in claim 1, wherein the first polyamine is spermine, and the second polyamine is selected from the group consisting of spermidine, putrescine, or mixtures thereof.

5. The method as recited in claim 4, wherein the spermine and the second polyamine are present in a ratio of about 1:9 to about 9:1.

6. The method as recited in claim 5, wherein the spermine and the second polyamine are present in a ratio of about 2:3 to about 3:2.

7. The method as recited in claim 1, wherein the polyunsaturated lipid comprises a polyunsaturated fatty acid.

8. The method as recited in claim 1, wherein the polyunsaturated lipid comprises an omega-3 fatty acid.

9. The method as recited in claim 1, wherein the polyunsaturated lipid is selected from the group consisting of eicosatetraenoic acid, docosahexaenoic acid, linolenic acid, and mixtures thereof.

10. The method as recited in claim 4, wherein the polyunsaturated lipid comprises a polyunsaturated fatty acid.

11. The method as recited in claim 4, wherein the polyunsaturated lipid comprises an omega-3 fatty acid.

12. The method as recited in claim 4, wherein the polyunsaturated lipid is selected from the group consisting of eicosatetraenoic acid, docosahexaenoic acid, linolenic acid, and mixtures thereof.

13. The method as recited in claim 1, wherein the polyunsaturated lipid comprises eicosapentaenoic acid.

14. The method as recited in claim 1, wherein the polyunsaturated lipid comprises linolenic acid.

15. A method to reduce the rate of oxidative rancidity of a material containing an omega-3 fatty acid comprising blending the omega-3 fatty acid containing material with spermine and a second polyamine, different from spermine, in amounts effective for reducing the rate of oxidative rancidity of the omega-3 fatty acid.

16. The method as recited in claim 15, wherein the blending comprises adding at least about 0.25 mM of each of spermine and the second polyamine.

17. The method as recited in claim 15, wherein the second polyamine is represented the general formula:

$$H_2N—[(CH_2)_p—(NH)_q—(CH_2)_r—(NH)_s—(CH_2)_t]_u—NH_2$$

wherein u is an integer of 1 to 5; p, r, and t independently are integers of 0 to 8, with the proviso that at least one of p, r, and t is greater than or equal to 2; wherein q and s independently are 0 or 1, with the proviso that u, p, r, t, q, and s being selected such that the formula represents a polyamine other than spermine.

18. The method as recited in claim 15, wherein the second polyamine is selected from the group consisting of spermidine, putrescine, or mixtures thereof.

19. The method as recited in claim 18, wherein the spermine and the second polyamine are present in a ratio of about 1:9 to about 9:1.

20. The method as recited in claim 19, wherein the spermine and the second polyamine are present in a ratio of about 2:3 to about 3:2.

21. The method as recited in claim 15, wherein the omega-3 fatty acid containing material contains at least about 5 percent omega-3 fatty acid, based on the total weight of the omega-3 fatty acid containing material.

22. The method as recited in claim 15, wherein the omega-3 fatty acid containing material contains at least about 95 percent omega-3 fatty acid, based on the total weight of the omega-3 fatty acid containing material.

23. The method as recited in claim 15, wherein the omega-3 fatty acid is selected from the group consisting of eicosatetraenoic acid, docosahexaenoic acid, linolenic acid, and mixtures thereof.

24. The method as recited in claim 14, wherein the polyunsaturated lipid comprises eicosapentaenoic acid.

25. The method as recited in claim 14, wherein the polyunsaturated lipid comprises linolenic acid.

26. A composition comprising a mixture of a polyunsaturated lipid; and a combination of polyamines including a first polyamine and a second polyamine, different from the first polyamine, in amounts effective for reducing the rate of oxidative rancidity of the polyunsaturated lipid.

27. The composition as recited in claim 26, wherein the composition has an average OSI value measured at 110° C. of at least about two fold higher than an average OSI value of the polyunsaturated lipid when treated with an equal total amount of the first or second polyamine ingredient alone.

28. The composition as recited in claim 26, wherein the first polyamine and second polyamine are independently represented the general formula:

$$H_2N—[(CH_2)_p—(NH)_q—(CH_2)_r—(NH)_s—(CH_2)_t]_u—NH_2$$

wherein u is an integer of 1 to 5; p, r, and t independently are integers of 0 to 8, with the proviso that at least one of p, r, and t is greater than or equal to 2; wherein q and s independently are 0 or 1, with the proviso that at least one of u, p, r, t, q, and s has a different integer value in the first polyamine than in the second polyamine.

29. The composition as recited in claim 28, wherein the composition contains at least about 0.25 mM of each of the first and second polyamines.

30. The composition as recited in claim 28, wherein the first polyamine is spermine, and the second polyamine is selected from the group consisting of spermidine, putrescine, or mixtures thereof.

31. The composition as recited in claim 30, wherein the spermine and the second polyamine are present in a ratio of about 1:9 to about 9:1.

32. The composition as recited in claim 31, wherein the spermine and the second polyamine are present in a ratio of about 2:3 to about 3:2.

33. The composition as recited in claim 26, wherein the polyunsaturated lipid comprises a polyunsaturated fatty acid.

34. The composition as recited in claim 26, wherein the polyunsaturated lipid comprises an omega-3 fatty acid.

35. The composition as recited in claim 26, wherein the polyunsaturated lipid is selected from the group consisting of eicosatetraenoic acid, docosahexaenoic acid, linolenic acid, and mixtures thereof.

36. The composition as recited in claim 26, wherein the polyunsaturated lipid comprises eicosapentaenoic acid.

37. The composition as recited in claim 26, wherein the polyunsaturated lipid comprises linolenic acid.

38. A composition comprising a mixture of a material containing an omega-3 fatty acid; and a combination of polyamines including spermine and a second polyamine, different from spermine, in amounts effective for reducing the rate of oxidative rancidity of the omega-3 fatty acid.

* * * * *